United States Patent [19]

Bruzzese et al.

[11] Patent Number: 5,472,705
[45] Date of Patent: Dec. 5, 1995

[54] PHARMACEUTICAL COMPOSITION CONTAINING ESTERS OF ω-3 POLYUNSATURATED ACIDS AND THEIR USE IN THE TOPICAL TREATMENT OF MORBID AFFECTIONS

[75] Inventors: Tiberio Bruzzese; Giovanni Mozzi; Remo Ruggeri, all of Milan, Italy

[73] Assignee: Prospa B.V., Amsterdam, Netherlands

[21] Appl. No.: 96,007

[22] Filed: Jul. 23, 1993

[30] Foreign Application Priority Data

Aug. 11, 1992 [NL] Netherlands ............................. 9201438

[51] Int. Cl.⁶ .............................. A61K 9/70; A61K 7/40
[52] U.S. Cl. ............................... 424/449; 424/59; 424/65; 424/78.06; 514/558; 514/560; 514/859; 514/860; 514/861; 514/863
[58] Field of Search ............................... 424/59, 65, 449, 424/78.06; 514/861, 863, 560, 859, 860, 558

[56] References Cited

U.S. PATENT DOCUMENTS

| | | | |
|---|---|---|---|
| 4,327,114 | 4/1982 | Brickl et al. | 424/331 |
| 4,515,810 | 5/1985 | Chow et al. | 514/530 |
| 4,710,383 | 12/1987 | Dick | 424/449 |
| 5,110,814 | 5/1992 | Engel et al. | 514/212 |

FOREIGN PATENT DOCUMENTS

| | | |
|---|---|---|
| 0454102A2 | 10/1991 | European Pat. Off. . |
| 3213744A1 | 11/1982 | Germany . |
| 4022815 | 1/1992 | Germany . |
| 1539270 | 1/1979 | United Kingdom . |
| 2142234 | 1/1985 | United Kingdom . |
| 2218904 | 11/1989 | United Kingdom . |

OTHER PUBLICATIONS

Patent Abstracts of Jaapan, vol. 15, No. 263 (C–0847) Jul. 4, 1991 & JP–A–30 90 046 (Mochida Pharmaceutical Co. Ltd.0 16 Apr. 1991.

Chemical Abstracts, vol. 115, No. 26, Dec. 30, 1991, Columbus, Ohio; abstract No. 287212x, 'transdermal pharmaceuticals containing eicosapentaenoic acid or its esters for treatment of skin diseases'.

*Primary Examiner*—Shailendra Kumar
*Attorney, Agent, or Firm*—Oblon, Spivak, McClelland, Maier, & Neustadt

[57] ABSTRACT

New pharmaceutical compositions for topical use containing esters of ω-3 polyunsaturated acids having a high concentration have been obtained. Such formulations have been added with phenolic antioxidants and with adjuvants.

The present formulations have been found clinically useful in the treatment of morbid affections, in particular in the treatment of psoriasis, phlebitis and the correlated pathologies.

14 Claims, No Drawings

PHARMACEUTICAL COMPOSITION CONTAINING ESTERS OF ω-3 POLYUNSATURATED ACIDS AND THEIR USE IN THE TOPICAL TREATMENT OF MORBID AFFECTIONS

The present invention relates to new pharmaceutical compositions containing esters of ω-3 polyunsaturated acids and to their use in the topical treatment of morbid affections.

The treatment of morbid affections, in particular of psoriasis, phlebitis and the related pathologies is effected, since a long time, by orally administering formulations comprising ω-3 polyunsaturated fatty acids or the esters thereof (usually the glyceride esters thereof) (Bittiner S. B. et al., Lancet, 378, 1, 1988; Ziboh V. A., Arch. Dermatol., 122, 1277, 1986; Maurice P. D. L. et al., Brit. J. Dermatol., 117, 599, 1987; Woodcock B. F. et al., Brit. Med. J., 288, 592, 1984 ).

A number of collateral and undesired effects may be however present using systemic administering route.

On the other hand, topical compositions containing said ω-3 polyunsaturated fatty acids or the esters thereof, have been, till now, never successfully prepared; in fact one of the main obstacles which has always prevented an effective topical use of said compounds and of their pharmaceutical formulations is their very unpleasant smell which derives from the oxidization, because of the atmospherical oxygen and of cutaneous enzymes, of the long chains thereof full of carbon to carbon double bonds which make up said ω-3 polyunsaturated fatty acids.

Creams, lotions or eels containing esters of polyunsaturated fatty acids, which are initially odourless or pleasantly perfumed, assume, because of such phenomenon some hours after their application, a very unpleasant and repellent smell, which they confer decidedly to the skin whereon they have been applied to and to those clothes eventually put into contact therewith.

The use of perfumes or any other deodorizing agent, even if intense and strong, is useless. In fact, upon application of the cream or of any other topical form to the skin, the perfume volatile components evaporate faster than the higher boiling esters of polyunsaturated fatty acids, which assume, in a very short time, the above said very unpleasant smell.

The use of aloe extracts has been recently suggested for the deodorization of the oils having natural origins (Bockow B. I. et al., WO 91/16914), but even this artifice has revealed itself absolutely uneffective.

The main purpose of the present invention is therefore to carry out a topical composition comprising esters of ω-3 polyunsaturated fatty acids as the active ingredient which permit to attain positive results avoiding the collateral and undesired effects always connected to the systemic administration of drugs and avoiding the generation of very unpleasant and repellent smells which would make otherwise topical formulations useless.

It has been surprisingly found that the addition of phenolic antioxidants in suitable amounts to topical compositions of the esters of ω-3 polyunsaturated fatty acids hinders the decomposition thereof and the generation of very unpleasant and repellent smells deriving therefrom.

In particular the present invention discloses a topical composition useful in the treatment of morbid affections comprising at least one $C_1$–$C_3$ alkyl ester of ω-3 polyunsaturated fatty acids as the active ingredient, characterized in that it comprises at least one phenolic antioxidant, whose weight percentage, with respect to said at least one ester, ranges between 0.3 and 5.0, preferably between 1.0 and 4.0 and that said at least one ester have a titer of at least 80%.

It has been also surprisingly found that the addition of triethylcitrate to the compositions of the present invention magnifies the activity of said phenolic antioxidants in inhibiting and hindering the generation of very unpleasant and repellent smells.

Therefore, the topical compositions of the present invention optionally comprise from 1% to 20% w/w of triethylcitrate with respect to said at least one ester of ω-3 polyunsaturated fatty acids, preferably from 5% to 15% w/w.

The esters of ω-3 polyunsaturated fatty acids particularly suitable for the scope of the present invention are $C_1$–$C_3$ alkyl esters, preferably ethyl esters selected from the group consisting of the esters of the cis-5, 8, 11, 14, 17 eicosapentaenoic acid (EPA) and of the cis-4, 7, 10, 13, 16, 19, docosahexaenoic acid (DHA).

The concentration of said esters of ω-3 polyunsaturated fatty acids in the compositions of the invention ranges from 10% to 40% w/w, preferably from 25% to 40% w/w.

The phenolic antioxidants suitable for the scope of the present invention are selected among ascorbyl palmitate, butylated hydroxytoluene, butylated hydroxyanisole and vitamin E; particularly suitable to the scope of the invention is the butylated hydroxyanisole.

Further, the phenolic antioxidants of the present invention are excellent deodorizing and stabilizing agents.

The pharmaceutical compositions which are the subject of the present invention are made dissolving the substances inhibiting and hindering the very unpleasant smells into the esters of ω-3 polyunsaturated fatty acids (which appear as oily liquids) and subsequently englobing the mixture so obtained in the vehicle constituting the pharmaceutical form, according to the usual practice of pharmaceutical technology.

To make clear the comprehension of the characteristics of the present invention, some embodiments will be hereinafter given by mere non limiting way of example.

EXAMPLE 1

A number of unpleasant smell inhibiting substances has been dissolved in the amounts set forth herebelow into an oily mixture of EPA and DHA ethylesters (overall titer ≧80%).

Some filter paper strips have been impregnated with solutions thereof, exposed to air in different climatic conditions and then assayed through an olfactory test by a group of examiners.

In the following table, the results expressed with a score ranging between 1 (very unpleasant smell) and 3 (odourless or having a pleasant smell) have been reported.

| | SMELL GENERATION AFTER AGEING OF THE EPA + DHA ETHYLESTERS ADMIXTURE | | | | | | | | |
|---|---|---|---|---|---|---|---|---|---|
| | | EXPOSITION AT 45° AND IN THE DARK | | | EXPOSITION AT RT AND IN THE LIGHT | | | | |
| COMPOSITION | INITIAL | 16 h | 24 h | 40 h | 24 h | 40 h | 64 h | 88 h | 150 h |
| EPA + DHA ethylesters mixture | 3 | 1 | 1 | 1 | 1 | 1 | 1 | 1 | 1 |
| +1% Vit. E | 3 | 3 | 3 | 2 | 3 | 3 | 3 | 3 | 1 |
| +1% A.P. | 3 | 2 | 1 | 1 | 3 | 1 | 1 | 1 | 1 |
| +1% BHA | 3 | 3 | 3 | 3 | 3 | 3 | 2 | 3 | 3 |
| +1% BHT | 3 | 3 | 1 | 1 | 3 | 3 | 2 | 2 | 3 |
| +10% TEC | 3 | 1 | 1 | 1 | 1 | 1 | 2 | 1 | 1 |
| +10% TEC + 1% BHT | 3 | 3 | 3 | 1 | 3 | 3 | 3 | 2 | 3 |

A.P. = Ascorbyl palmitate
BHA = Butylated Hydroxyanisole
BHT = Butylated Hydroxytoluene
TEC = Triethyl Citrate

EXAMPLE 2

Operating in a way analogous to that one described in the Example 1, a number of different amounts of butylated hydroxyanisole (BHA) and Vitamin E have been assayed.

| | SMELL GENERATION AFTER AGEING OF THE EPA + DHA ETHYLESTERS MIXTURE | | | | | | | | |
|---|---|---|---|---|---|---|---|---|---|
| | | Exposition at 45° and in the dark | | | Exposition at RT and in the light | | | | |
| Composition | Initial | 24 h | 48 h | 56 h | 24 h | 48 h | 56 h | 120 h | 144 h |
| EPA + DHA ethylesters mixture | 3 | 1 | 1 | 1 | 1 | 1 | 1 | 1 | 1 |
| +0.03% BHA | 3 | 1 | 1 | 1 | 3 | 3 | 3 | 1 | 1 |
| +0.1% BHA | 3 | 1 | 1 | 1 | 3 | 3 | 3 | 1 | 1 |
| +0.5% BHA | 3 | 3 | 2 | 1 | 3 | 3 | 3 | 3 | 3 |
| +1% BHA | 3 | 3 | 2 | 1 | 3 | 3 | 3 | 3 | 3 |
| +3% BHA | 3 | 3 | 3 | 3 | 3 | 3 | 3 | 3 | 3 |
| +0.03% Vit. E | 3 | 1 | 1 | 1 | 3 | 1 | 1 | 1 | 1 |
| +0.1% Vit. E | 3 | 1 | 1 | 1 | 3 | 1 | 1 | 1 | 1 |
| +0.5% Vit. E | 3 | 2 | 1 | 1 | 3 | 2 | 3 | 1 | 1 |
| +1% Vit. E | 3 | 3 | 2 | 1 | 3 | 3 | 3 | 3 | 1 |
| +3% Vit. E | 3 | 3 | 3 | 3 | 3 | 3 | 3 | 3 | 3 |

EXAMPLE 3

| | | |
|---|---|---|
| EPA + DHA ethylesters mixture (overall titer ≧80%) | g | 30 |
| Butyl hydroxyanisole | g | 1 |
| Mixture of saturated fatty acids glycerides and poly oxyethylenated saturated fatty acids | g | 12 |
| Carbopol 974P | g | 0.3 |
| Triethanolamine | g | 0.3 |
| Methyl p-hydroxybenzoate | g | 0.12 |
| Ethyl p-hydroxybenzoate | g | 0.05 |
| Propyl p-hydroxybenzoate | g | 0.03 |
| Perfume and depurated water | q.s. to g | 100 |

Dissolve in the boiling water the p-hydroxybenzoates, thermostat at 75° C. and dissolve Carbopol therein. Contemporaneously, melt at about 75° C. the saturated fatty acids glycerides and polyoxyethylenated saturated fatty acids mixture and add, while stirring, the aqueous phase previously prepared.

Cool at about 60° C. and add the EPA and DHA ethylesters mixture, wherein the butylated hydroxyanisole has been previously dissolved, to the emulsion.

Add the triethanolamine to the so obtained mixture, cool at about 40° C., add the perfume and cool at room temperature.

EXAMPLE 4

| | | |
|---|---|---|
| EPA and DHA ethylesters mixture (overall titer ≧80%) | g | 30 |
| Vitamin E | g | 1 |
| Mixture of saturated fatty acids glycerides and polyoxyethylenated saturated fatty acids | g | 12 |
| Carbopol 974 P | g | 0.3 |
| Triethanolamine | g | 0.3 |
| Methyl p-hydroxybenzoate | g | 0.12 |
| Ethyl p-hydroxybenzoate | g | 0.05 |
| Propyl p-hydroxybenzoate | g | 0.03 |
| Perfume and depurated water | q.s. to g | 100 |

Vitamin E is dissolved into the EPA and DHA ethylesters mixture before of the addition to the emulsion, the preparation of the present formulation being, for the rest, substantially analogous to that one of the Example 3.

EXAMPLE 5

| | | |
|---|---|---|
| EPA ethylester (titer ≧80%) | g | 10 |
| Butylated hydroxy toluene | g | 0.1 |
| Triethylcitrate | g | 1 |
| Mixture of saturated fatty acids glycerides and polyoxyethylenated saturated fatty acids | g | 6 |
| Carbopol 974 P | g | 0.5 |
| Triethanolamine | g | 0.5 |
| Methyl p-hydroxybenzoate | g | 0.12 |
| Ethyl p-hydroxybenzoate | g | 0.05 |
| Propyl p-hydroxybenzoate | g | 0.03 |
| Perfume and depurated water | q.s. to g | 100 |

The butylated hydroxyanisole and the triethylcitrate are dissolved into the EPA ethylester before of the addition to the emulsion, the preparation of the present formulation being, for the rest, substantially analogous to that one of the Example 3.

EXAMPLE 6

| | | |
|---|---|---|
| DHA ethylester (titer ≧80%) | g | 40 |
| Buthylated hydroxyanisole | g | 2 |
| Mixture of saturated fatty acids glycerides and polyoxyethylenated saturated fatty acids | g | 12 |
| Carbopol 974P | g | 0.3 |
| Triethanolamine | g | 0.3 |
| Methyl p-hyroxybenzoate | g | 0.12 |
| Ethyl p-hydroxybenzoate | g | 0.05 |
| Propyl p-hydroxybenzoate | g | 0.03 |
| Perfume and depurated water | q.s. to g | 100 |

The preparation is analogous to that one of the Example 3.

EXAMPLE 7

Using the procedures described in the foregoing examples, n.5 creams have been prepared having the following formulae:

Some filter paper strips, smeared with the various creams, have been exposed to the air in different climatic conditions and, then, assayed by an olfactory test by a group of examiners. The results expressed by a score ranging from 1 (very unpleasant smell) to 3 (odourless or having a pleasant smell) have been reported in the following table.

| SMELL GENERATION AFTER AGEING OF THE CREAM | | | | |
|---|---|---|---|---|
| | | Exposition at 45° C. and in the dark | | Exposition at RT and in the light |
| Cream formula | Initial | 34 h | 50 h | 96 h | 120 h |
| Control | 3 | 1 | 1 | 1 | 1 |
| BHT | 3 | 2 | 1 | 3 | 3 |
| TEC + BHT | 3 | 3 | 3 | 3 | 3 |
| A1 | 3 | 1 | 1 | — | — |
| A2 | 3 | 1 | 1 | — | — |

EXAMPLE 8

Using the usual procedures n.5 creams have been prepared having the following formulae:

| | | I (reference) | II (BHT) | III (TEC + BHT) | IV (A1) | V (A2) |
|---|---|---|---|---|---|---|
| EPA AND DHA ethylesters (overall titer ≧80%) | g | 30 | 30 | 30 | 30 | 30 |
| Butylated hydroxytoluene | g | — | 0.3 | 0.3 | — | — |
| Triethylcitrate | g | — | — | 3 | — | — |
| Aloe powder | — | — | — | — | 2 | — |
| Aloe sol. 10:1 | g | — | — | — | — | 15 |
| Mixture of saturated fatty acids glycerides and poly-oxyethylenated saturated fatty acids | g | 12 | 12 | 12 | 12 | 12 |
| Carbopol 974P | g | 0.3 | 0.3 | 0.3 | 0.3 | 0.3 |
| Triethanolamine | g | 0.3 | 0.3 | 0.3 | 0.3 | 0.3 |
| Methyl p-hydroxybenzoate | g | 0.12 | 0.12 | 0.12 | 0.12 | 0.12 |
| Ethyl p-hydroxybenzoate | g | 0.05 | 0.05 | 0.05 | 0.05 | 0.05 |
| Propyl p-hydroxybenzoate | g | 0.03 | 0.03 | 0.03 | 0.03 | 0.03 |
| Perfume and depurated water | | | | q.s. to 100 g | | |

|  | | I (referim.) | II (0.3% BHA) | III (1% BHA) | IV (0.3% Vit. E) | V (1% Vit. E) |
|---|---|---|---|---|---|---|
| EPA and DHA ethylesters mixture (overall titer ≧80%) | g | 30 | 30 | 30 | 30 | 30 |
| Butylated hydroxyanisole | g | — | 0.3 | 1 | — | — |
| Vitamin E | g | — | — | — | 0.3 | 1 |
| Mixture of saturated fatty acids glycerides and polyoxyethylenated saturated fatty acids | g | 12 | 12 | 12 | 12 | 12 |
| Carbopol 974P | g | 0.3 | 0.3 | 0.3 | 0.3 | 0.3 |
| Triethanolamine | g | 0.3 | 0.3 | 0.3 | 0.3 | 0.3 |
| Methyl p-hydroxybenzoate | g | 0.12 | 0.12 | 0.12 | 0.12 | 0.12 |
| Ethyl p-hydroxybenzoate | g | 0.05 | 0.05 | 0.05 | 0.05 | 0.05 |
| Propil p-hydroxybenzoate | g | 0.03 | 0.03 | 0.03 | 0.03 | 0.03 |
| Perfume and depurated water | | | | q.s. to 100 g | | |

Some filter paper strips have been smeared with cream and assayed after exposition to the air, analogously to what has been done in the Example 7.

The results have been reported in the following table.

| SMELL GENERATION AFTER AGEING OF THE CREAM | | | | | | |
|---|---|---|---|---|---|---|
| | Exposition at 75° C. and in the dark | Exposition at 45° C. and in the dark | | Exposition at RT and in the light | | |
| Cream formula | Initial  6h | 48 h | 72 h | 144 h | 216 h | 240 h |
| Control | 3   1 | 2 | 1 | 1 | 1 | 1 |
| 0.3% BHA | 3   3 | 2 | 2 | 3 | 3 | 3 |
| 1% BHA | 3   3 | 3 | 3 | 3 | 3 | 3 |
| 0.3% Vit. E | 3   3 | 2 | 2 | 3 | 1 | 1 |
| 1% Vit. E | 3   2 | 3 | 3 | 2 | 3 | 3 |

EXAMPLE 9

8 patients afflicted with psoriasis, in various parts of their body, have been treated for four weeks with a cream containing a 30% mixture of EPA and DHA ethylesters (having an overall titer ≧80%), having a formulation that is identical to that one of the Example 3.

As to erythema and desquamation, a score ranging from 1 to 5 has been assigned to each patient at the beginning and at the end of the treatment.

A higher score corresponded to a greater seriousness of the symptoms.

The mean of the scores and the corresponding standard deviation thereof have been reported in the following table at the beginning and at the end of the treatment.

| | Desquamation | | Erythema | |
|---|---|---|---|---|
| Treatment phase | mean | s.d. | mean | s.d. |
| Beginning | 3.1 | 0.64 | 3.4 | 0.74 |
| End | 1.9 | 0.99 | 2.0 | 0.93 |

The means obtained have been elaborated according to the t Student test and the respective decreases thereof, because of the treatment, have turned out to be highly significant (P<0.01) for what concerns either desquamation or erythema, thus confirming the effectiveness of the drug used.

EXAMPLE 10

6 patients afflicted with phlebitis have been treated for three weeks with a cream containing a 30% EPA and DHA ethylesters admixture (having an overall titer≧80%), having a formulation identical to that one of the Example 3.

The presence of ulcers and, by a score ranging from 0 to 3, the seriousness of the other components of the symptomatology: pain, oedema and cyanosis, have been registered for each patient at the beginning and at the end of the treatment.

A higher score corresponded to a greater seriousness of the symptoms.

The relevant results are reported in the following table:

| Patient Nr. | Ulcer begin. | Ulcer end | Pain begin. | Pain end | Oedema begin. | Oedema end | Cyanosis begin. | Cyanosis end |
|---|---|---|---|---|---|---|---|---|
| 1 | YES | NO | 2 | 0 | 2 | 0 | 3 | 1 |
| 2 | NO | NO | 3 | 1 | 2 | 1 | 3 | 2 |
| 3 | YES | NO | 3 | 1 | 3 | 1 | 2 | 0 |
| 4 | YES | NO | 2 | 0 | 2 | 0 | 2 | 0 |
| 5 | YES | YES | 3 | 2 | 2 | 1 | 3 | 1 |
| 6 | NO | NO | 2 | 0 | 2 | 0 | 2 | 0 |

The improvements attained because of the treatment which has been set up are evident.

We claim:

1. A topical composition for treating morbid affections, comprising:

(a) 25% to 40% by weight of at least one $C_{1-3}$ alkyl ester of a ω-3 polyunsaturated fatty acid selected from the group consisting of a $C_{1-3}$ alkyl ester of cis-5, 8, 11, 14, 17-eicosapentaenoic acid and a $C_{1-3}$ alkyl ester of cis-4, 7, 10, 13, 16, 19-docosahexaenoic acid, wherein said at least one $C_{1-3}$ alkyl ester of a ω-3 polyunsaturated fatty acid has a titer of at least 80%;

(b) 1% to 4% by weight with respect to said at least one $C_{1-3}$ alkyl ester (a) of at least one phenolic antioxidant; and (c) 5% to 15% by weight with respect to said at least one $C_{1-3}$ alkyl ester (a) of triethylcitrate.

2. A topical composition according to claims 1, characterized in that said $C_1$–$C_3$ alkyl ester of a ω-3 polyunsaturated fatty acids is an ethyl ester.

3. A topical composition according to one of claim 2 or 1, characterized in that said at least one phenolic antioxidant is selected from the group consisting of butylated hydroxyanisole, butylated hydroxytoluene and vitamin E.

4. A topical composition according to claim 1, characterized in that said phenolic antioxidant is the butylated hydroxy anisole.

5. A topical composition according to one of claims 2, 4 or 1, characterized in that it is active against psoriasis.

6. A topical composition according to one of claims 2, 4 or 1, characterized in that it is active against phlebitis.

7. A topical composition according to one of claims 2, 4 or 1, characterized in that it is active against atopic eczema.

8. The topical composition according to claim 3, wherein said composition is active against psoriasis.

9. The topical composition according to claim 3, wherein said composition is active against phlebitis.

10. The topical composition according to claim 5, wherein said composition is active against phlebitis.

11. The topical composition according to claim 3, wherein said composition is active against atopic eczema.

12. The topical composition according to claim 5, wherein said composition is active against atopic eczema.

13. The topical composition according to claim 6, wherein said composition is active against atopic eczema.

14. A method of treating a morbid affection comprising topically treating the affection with the composition of claim 1.

* * * * *